United States Patent
Flores

(10) Patent No.: US 9,498,575 B2
(45) Date of Patent: Nov. 22, 2016

(54) SUBSTANCE DELIVERY DEVICES, SYSTEMS AND METHODS

(71) Applicant: MRI Interventions, Inc., Memphis, TN (US)

(72) Inventor: Jesse Flores, Perris, CA (US)

(73) Assignee: MRI Interventions, Inc., Irvine, CA (US)

( * ) Notice: Subject to any disclaimer, the term of this patent is extended or adjusted under 35 U.S.C. 154(b) by 207 days.

(21) Appl. No.: 14/206,039

(22) Filed: Mar. 12, 2014

(65) Prior Publication Data
US 2014/0276614 A1    Sep. 18, 2014

Related U.S. Application Data

(60) Provisional application No. 61/784,408, filed on Mar. 14, 2013.

(51) Int. Cl.
*A61M 37/00*    (2006.01)
*A61M 5/145*    (2006.01)
*A61M 5/142*    (2006.01)
*A61M 5/00*    (2006.01)

(52) U.S. Cl.
CPC ....... *A61M 5/14526* (2013.01); *A61M 5/1456* (2013.01); *A61M 5/14212* (2013.01); *A61M 5/007* (2013.01); *A61M 2205/057* (2013.01); *A61M 2210/06* (2013.01)

(58) Field of Classification Search
CPC .............. A61M 5/14593; A61M 5/14526; A61M 2005/14513
See application file for complete search history.

(56) References Cited

U.S. PATENT DOCUMENTS

| | | | |
|---|---|---|---|
| 2,841,144 A | * | 7/1958 | Cohen .................. A61M 5/286 604/198 |
| 6,026,316 A | | 2/2000 | Kucharczyk et al. |
| 6,050,992 A | | 4/2000 | Nichols |
| 6,167,311 A | | 12/2000 | Rezai |
| 6,356,786 B1 | | 3/2002 | Rezai et al. |
| 6,405,079 B1 | | 6/2002 | Ansarinia |
| 6,438,423 B1 | | 8/2002 | Rezai et al. |
| 6,526,318 B1 | | 2/2003 | Ansarinia |
| 6,539,263 B1 | | 3/2003 | Schiff et al. |
| 6,609,030 B1 | | 8/2003 | Rezai et al. |
| 6,708,064 B2 | | 3/2004 | Rezai |
| 8,374,677 B2 | | 2/2013 | Piferi et al. |
| 2003/0105430 A1 | * | 6/2003 | Lavi .................... A61M 5/2033 604/136 |

(Continued)

*Primary Examiner* — Emily Schmidt
(74) *Attorney, Agent, or Firm* — Myers Bigel, P.A.

(57) ABSTRACT

A substance delivery device includes an elongated tubular body having opposing proximal and distal ends, a plunger assembly slidably received within the tubular body at the proximal end thereof, and a hollow needle secured within the tubular body at the distal end thereof. The tubular body includes a longitudinal opening located between the proximal and distal ends that is adapted to allow a substance cartridge to be inserted within the tubular body. The plunger assembly includes a plunger that is in slideable sealing engagement with an inside wall of the tubular body, an engagement head positioned proximate an opposite end of the longitudinal opening, and a rod extending between and connecting the plunger and engagement head.

20 Claims, 11 Drawing Sheets

(56) References Cited

U.S. PATENT DOCUMENTS

| | | | |
|---|---|---|---|
| 2005/0245881 A1* | 11/2005 | Meyer | A61F 9/0017 604/232 |
| 2006/0200083 A1* | 9/2006 | Freyman | A61M 5/14526 604/181 |
| 2008/0086111 A1* | 4/2008 | Cowan | A61M 5/14216 604/522 |
| 2010/0114059 A1* | 5/2010 | Hiniduma-Lokuge | A61M 5/1452 604/500 |
| 2010/0152661 A1* | 6/2010 | Clavadetscher | A61M 5/1413 604/150 |
| 2010/0305507 A1* | 12/2010 | Duncan | A61M 5/14526 604/121 |
| 2012/0191102 A1* | 7/2012 | Matsumoto | A61B 17/8822 606/94 |
| 2013/0030408 A1 | 1/2013 | Piferi et al. | |

* cited by examiner

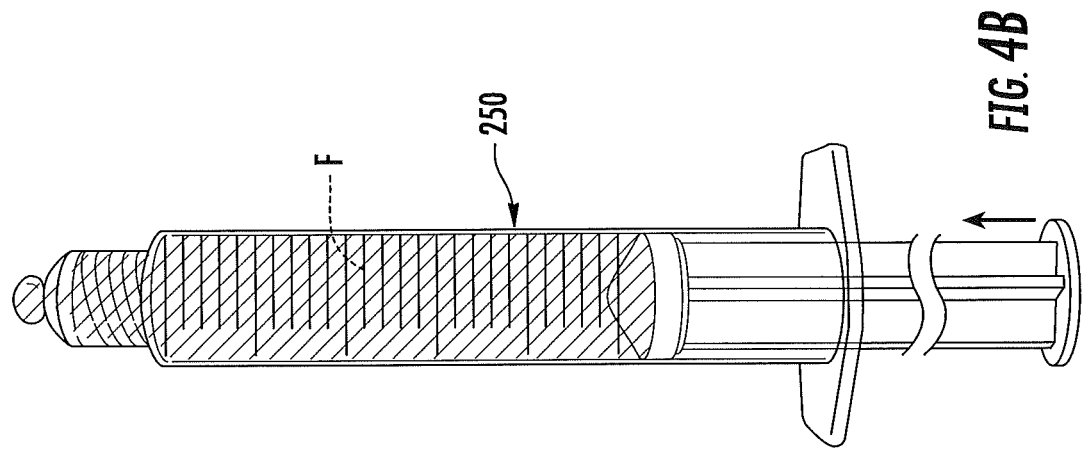
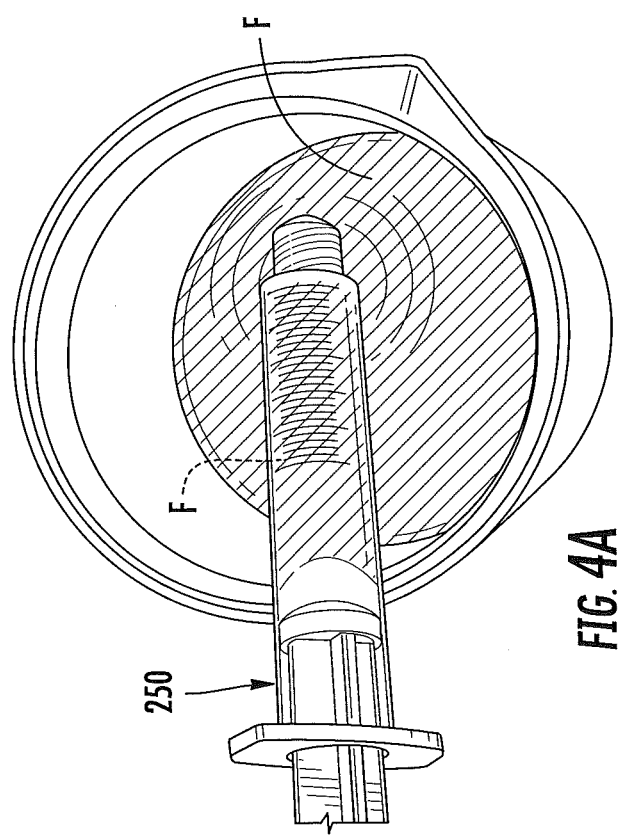

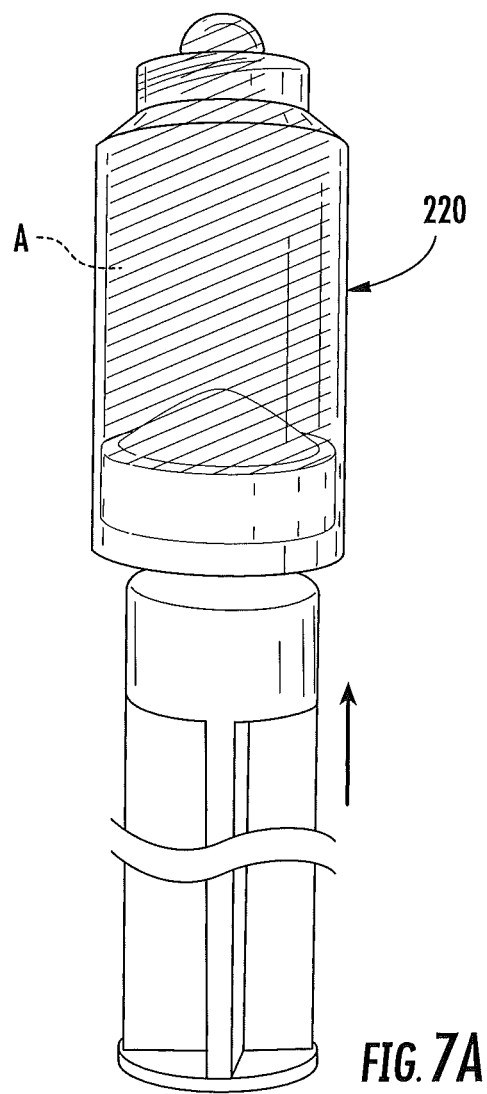
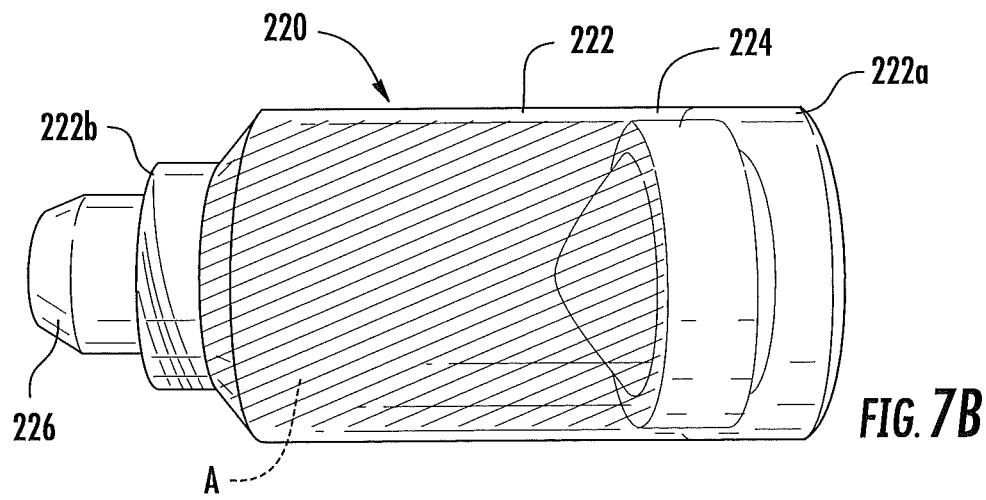

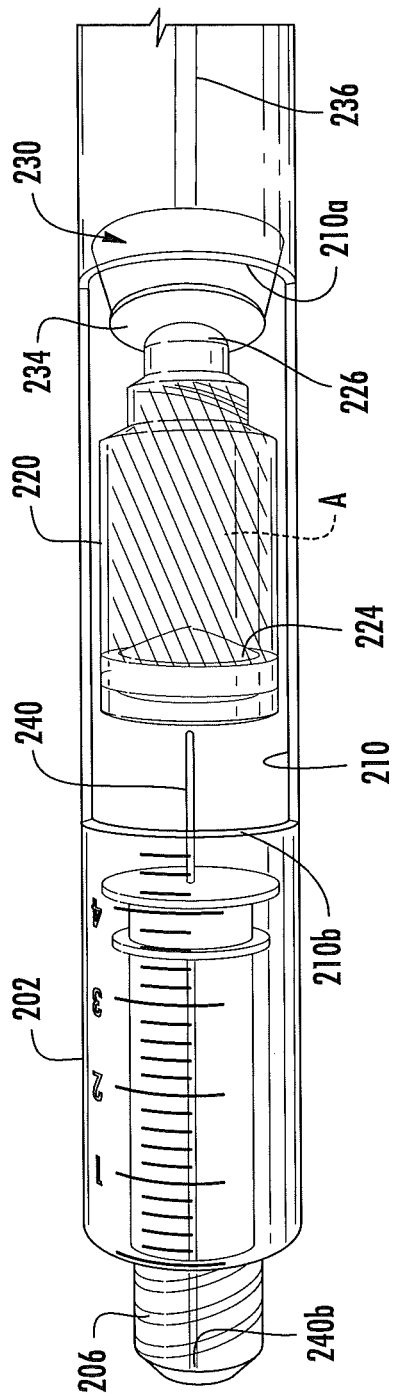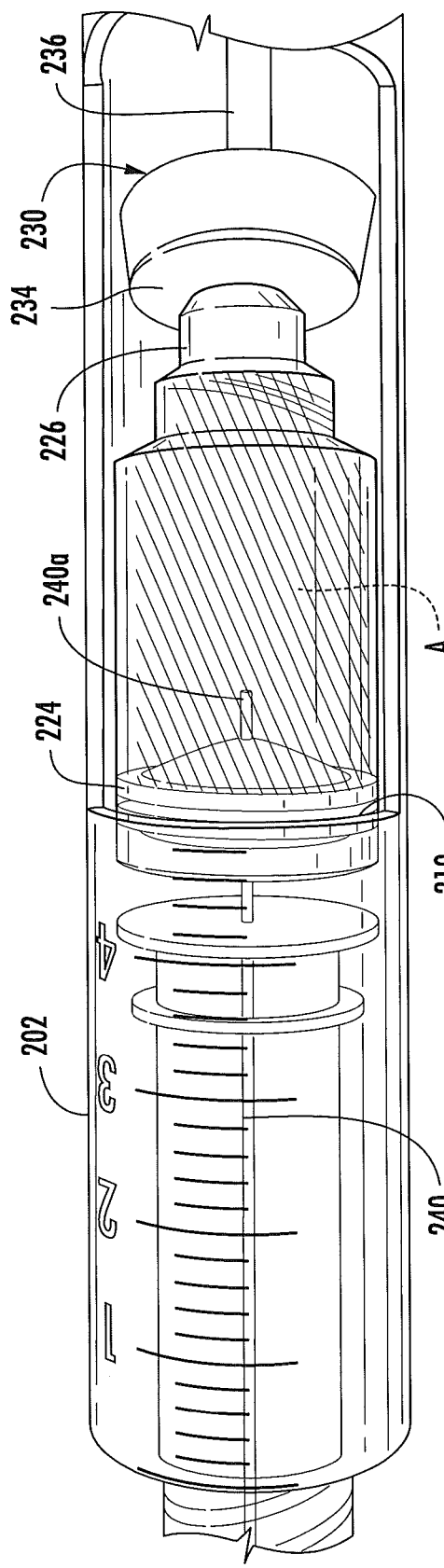

SUBSTANCE DELIVERY DEVICES, SYSTEMS AND METHODS

RELATED APPLICATION

This application claims the benefit of and priority to U.S. Provisional Patent Application No. 61/784,408 filed Mar. 14, 2013, the disclosure of which is incorporated herein by reference as if set forth in its entirety.

FIELD OF THE INVENTION

The present invention relates generally to medical devices and systems and, more particularly, to devices and systems for delivering substances in vivo, and may be particularly suitable for MRI-guided procedures.

BACKGROUND

Various therapeutic and diagnostic procedures require that a substance be infused into a prescribed region of a patient, such as into a target deep brain location in the patient's brain, using a delivery cannula. It may be important or critical that the substance be delivered with high accuracy to the target region in the patient and without undue trauma to the patient. MRI-guided deliveries typically employ long lengths of tubing resulting in relatively large "dead spaces" that often result in a volume of medical substance that may be wasted or unused. Because of the high cost of such medical substances, it may be desirable to reduce the amount of substance that is wasted or unused.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a substance delivery device includes a tubular body having opposing proximal and distal ends, a plunger assembly slidably received within the tubular body proximate the proximal end thereof, and a hollow needle secured within the tubular body proximate the distal end thereof. The tubular body includes a longitudinal opening located between the proximal and distal ends that allows a substance cartridge (single use or multiple use) to be inserted within the tubular body. The plunger assembly includes a plunger that is in slideable sealing engagement with an inside wall of the tubular body, an engagement head positioned proximate an opposite end of the longitudinal opening, and a rod extending between and connecting the plunger and engagement head.

According to some embodiments of the present invention, a system for delivering a substance to a patient includes a substance delivery device, and a syringe in communication with the substance delivery device for causing a substance containing cartridge disposed within the substance delivery device to release the substance from the cartridge. The substance delivery device includes a tubular body having opposing proximal and distal ends, a plunger assembly slidably received within the tubular body proximate the proximal end thereof, and a hollow needle secured within the tubular body proximate the distal end thereof. The tubular body includes a longitudinal opening located between the proximal and distal ends that allows a substance cartridge to be inserted into the tubular body. The plunger assembly includes a plunger that is in slideable sealing engagement with an inside wall of the tubular body, an engagement head positioned proximate an opposite end of the longitudinal opening, and a rod extending between and connecting the plunger and engagement head. The syringe is in fluid communication with the tubular body proximal end and contains a slave fluid. User activation of the syringe causes the slave fluid to move a substance cartridge positioned within the tubular body via the plunger assembly such that the substance cartridge is pierced by the piercing end of the hollow needle.

In some embodiments, the system includes a cannula that is in fluid communication with the hollow needle, typically via tubing connected to the tubular body distal end, although tubing is not required. The cannula is adapted to transfer the substance in the cartridge to a selected region in a patient. In some embodiments, the cannula is MRI-compatible.

In some embodiments, the system includes a pump adapted to activate the syringe and to cause the slave fluid to move the substance cartridge such that the cartridge is pierced by the needle and the substance is forced out of the cartridge.

According to some embodiments of the present invention, a substance cartridge includes a tubular body having opposing proximal and distal ends. A diaphragm is in slideable sealing engagement with an inside wall of the tubular body. The diaphragm is configured to be releasably engaged by a member inserted through the tubular body proximal end, and is movable between the tubular body proximal and distal ends via the member. In some embodiments, the diaphragm includes a threaded portion configured to be threadingly engaged by the member.

In some embodiments, the tubular body distal end comprises a threaded portion. A cap may be threadingly secured to the distal end. To fill the cartridge with a substance, the cap is removed and a needle is secured to the distal end. The substance is drawn into the cartridge through the needle by submersing the needle in the substance and then moving the diaphragm from the tubular body distal end to the proximal end via the member.

In some embodiments, the tubular body and diaphragm are MRI-compatible.

According to some embodiments of the present invention, a method for delivering a substance to a patient in an MRI-guided surgical procedure includes inserting a cannula into a selected region of the patient, wherein the cannula comprises a lumen that is in fluid communication with a substance delivery device containing the substance; and transferring the substance from the substance delivery device to the selected region through the lumen via a slave fluid.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIGS. 4A-4C and 5A-5B illustrate exemplary operations for filling a syringe and tubing with a slave fluid that are to be attached to the substance delivery device of FIG. 3.

FIGS. 6A-6C and 7A-7B illustrate exemplary operations for filling a cartridge with a substance that is to be delivered into a patient.

FIG. 7C illustrates the filled cartridge of FIG. 7B inserted within the substance delivery device of FIG. 3.

FIG. 8 is an enlarged partial view of the substance delivery device of FIG. 7C illustrating that the plunger assembly has moved the cartridge such that the piercing end of the needle in the substance delivery device has penetrated the cartridge diaphragm to release the substance from the cartridge.

DETAILED DESCRIPTION

Figure 1:
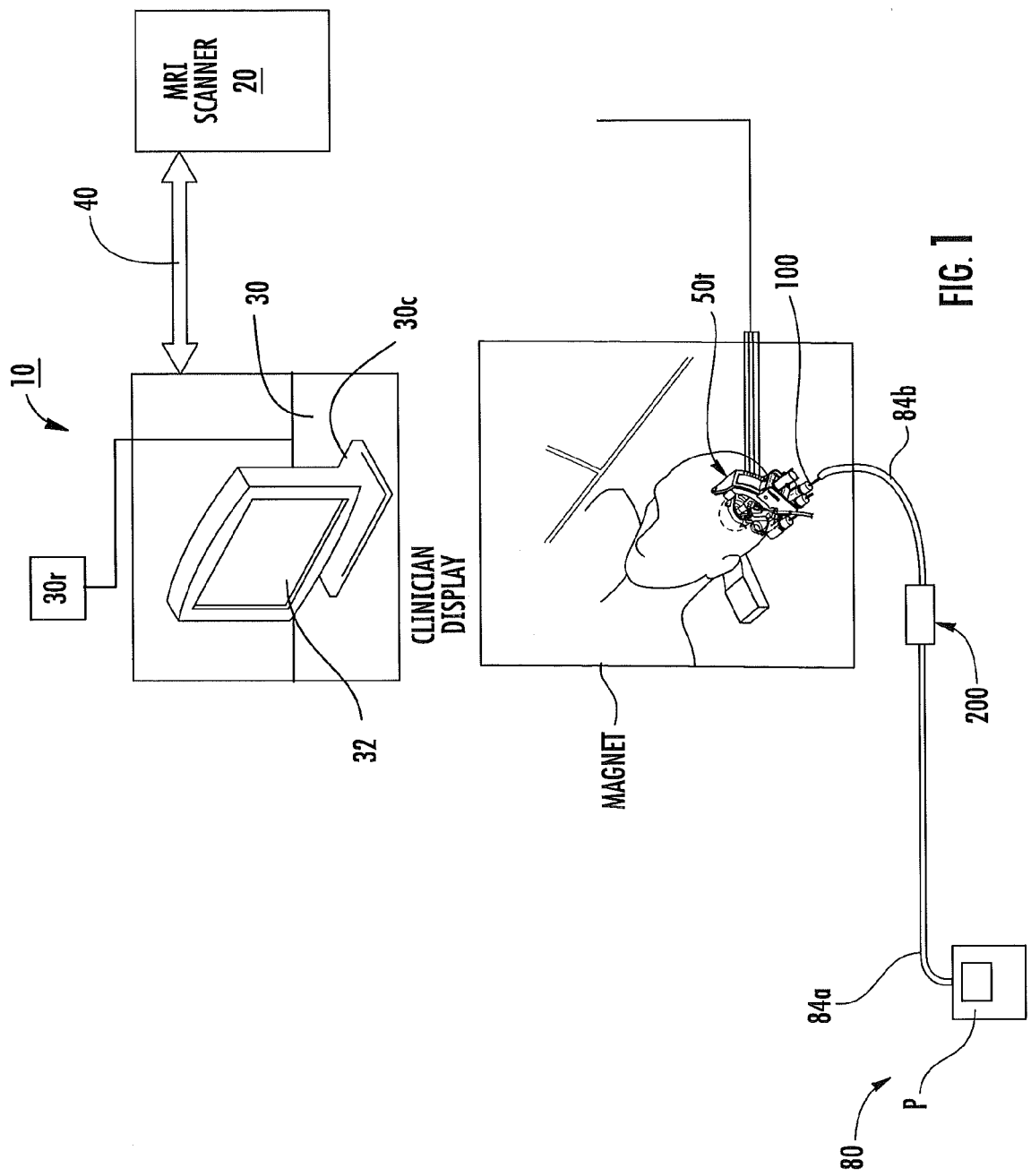
FIG. 1 is a schematic illustration of an MRI-guided interventional system in which embodiments of the present invention may be utilized.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "about", as used herein with respect to a value or number, means that the value or number can vary by +/− twenty percent (20%).

The term "MRI visible" means that a device is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MRI compatible" means that a device is safe for use in an MRI environment and/or can operate as intended in an MRI environment without generating MR signal artifacts, and, as such, if residing within the high-field strength region of the magnetic field, is typically made of a non-ferromagnetic MRI compatible material(s) suitable to reside and/or operate in a high magnetic field environment.

The term "high-magnetic field" refers to field strengths above about 0.5 T (Tesla), typically above 1.0 T, and more typically between about 1.5 T and 10 T.

The term "near real time" refers to both low latency and high frame rate. Latency is generally measured as the time from when an event occurs to display of the event (total processing time). For tracking, the frame rate can range from between about 100 fps to the imaging frame rate. In some embodiments, the tracking is updated at the imaging frame rate. For near 'real-time' imaging, the frame rate is typically between about 1 fps to about 20 fps, and in some embodiments, between about 3 fps to about 7 fps. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., stylet, catheter, etc.) and the near RT MR image(s) are generated.

The terms "surgical cannula" and "cannula", as used herein, are interchangeable and refer to an intrabody cannula used to transfer a substance to a target intrabody location.

The term "sterile", as used herein, means that a device, kit, and/or packaging meets medical/surgical cleanliness guidelines, and typically is free from live bacteria or other microorganisms.

Embodiments of the present invention can be utilized with various diagnostic or interventional devices and/or therapies to any desired internal region of the body or object using MRI and/or in an MRI scanner or MRI interventional suite. The object can be any object, and may be particularly suitable for animal and/or human subjects. Some embodiments can be configured to deliver therapies that stimulate a desired region of the sympathetic nerve chain. Other uses inside or outside the brain include stem cell placement, gene therapy or drug delivery for treating physiological conditions, chemotherapy and drugs replicating therapy drugs. Some embodiments can be used to treat tumors.

The term "substance", as used herein, refers to a liquid for treating or facilitating diagnosis of a condition and can include bions, stem cells or other target cells to site-specific regions in the body, such as neurological target sites and the like. In some embodiments, stem cells and/or other cardio-rebuilding cells or products can be delivered into cardiac tissue, such as a heart wall via a minimally invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

Embodiments of the present invention will now be described in further detail below with reference to the figures. FIG. 1 illustrates an MRI-guided interventional system 10 with an MRI scanner 20, a clinician workstation 30 with at least one circuit 30c, at least one display 32, an MRI compatible trajectory guide 50t, a depth stop 70 (FIG. 2), and a fluid substance delivery system 80. The fluid substance delivery system 80 includes an MRI-compatible intrabody surgical or delivery cannula 100, an infusion pump P, a substance delivery device 200 that is configured to receive a substance cartridge (220, FIGS. 6A-6C, FIGS. 7A-7C, FIG. 8), and connecting tubing 84a, 84b. The system 10 can be configured to render or generate real time visualizations of the target anatomical space using MRI image data and predefined data of at least one surgical tool to segment the image data and place the trajectory guide 50t and the cannula 100 in the rendered visualization in the correct orientation and position in 3D space, anatomically registered to a patient. The trajectory guide 50t and the cannula 100 can include or cooperate with tracking, monitoring and/or interventional components.

An exemplary trajectory guide 50t is illustrated in FIG. 1 in position on a patient. The trajectory guide 50t typically provides X-Y adjustment and pitch and roll adjustment in order to accurately position the cannula 100 at a desired location within a patient. For additional discussion of suitable trajectory guides, see, U.S. Pat. No. 8,374,677, the contents of which are hereby incorporated by reference as if recited in full herein.

The tools of the system 10, including the cannula 100 and substance delivery device 200 (described below with respect to FIGS. 3-10) associated with the cannula 100, can be provided as a sterile kit (typically as single-use disposable hardware) or in other groups or sub-groups or even individually, typically provided in suitable sterile packaging.

Figure 2:
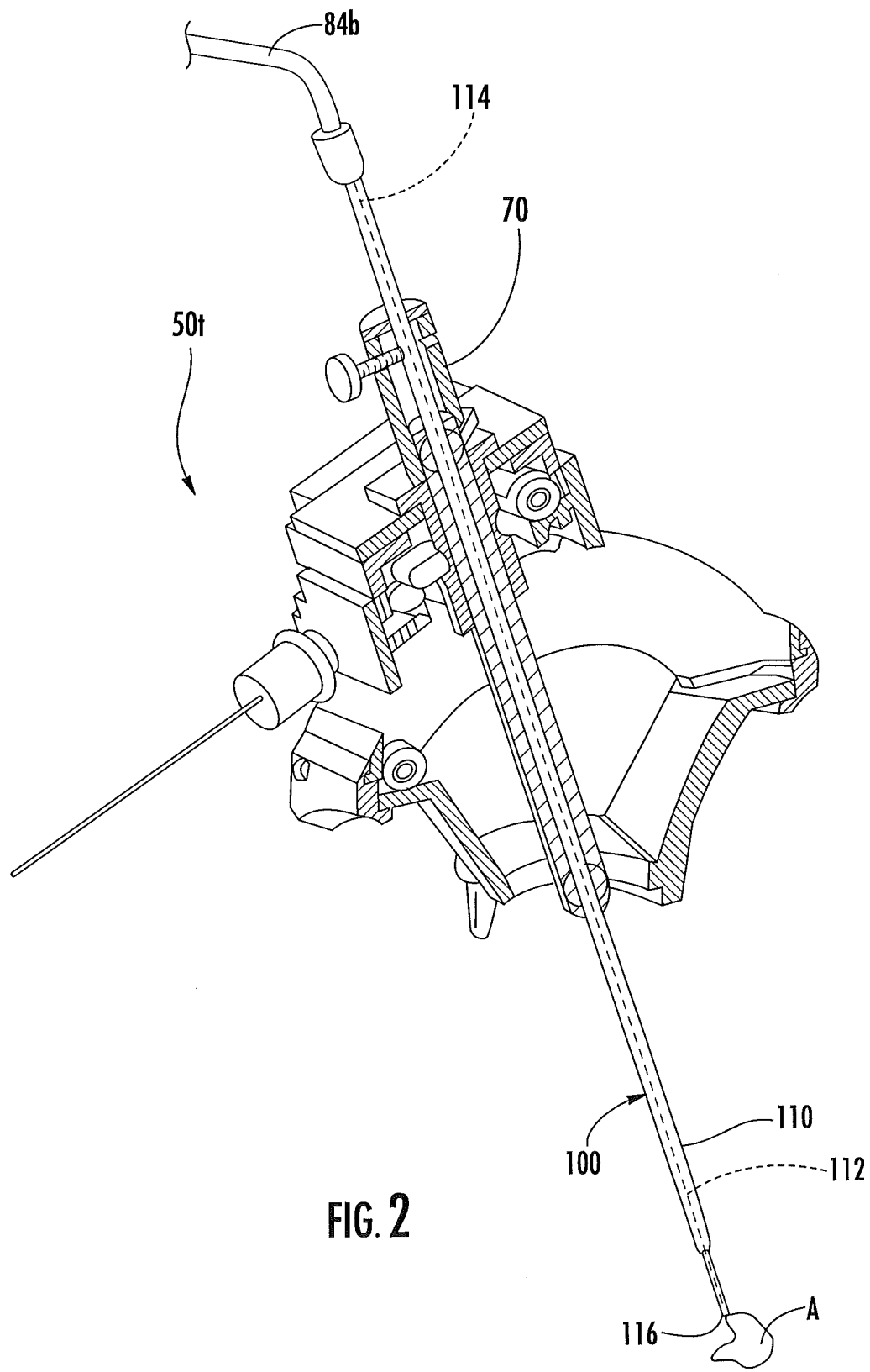
FIG. 2 is a sectional view of the trajectory guide of the MRI-guided system of FIG. 1 with a surgical cannula for transferring a substance (e.g., an infusate, etc.) to a patient.

The cannula 100 can be configured to flowably introduce and/or inject a desired therapy substance (e.g., antigen, gene therapy, chemotherapy or stem-cell or other therapy type). The cannula 100 as shown in FIG. 2, is an exemplary cannula and various other types of cannulas can be utilized with a substance delivery device 200, according to embodiments of the present invention. The illustrated cannula 100 includes a cannula body 110 defining at least one longitudinally extending lumen 112, an inlet port 114 and at least one exit port 116. The cannula 100 typically is formed of an MRI-compatible, MRI-visible material such as ceramic. For additional discussion of exemplary cannulas that can be used with embodiments of the present invention, see, U.S. Patent Application Publication No. US 2013/0030408, the contents of which are hereby incorporated by reference as if recited in full herein.

Figure 10:
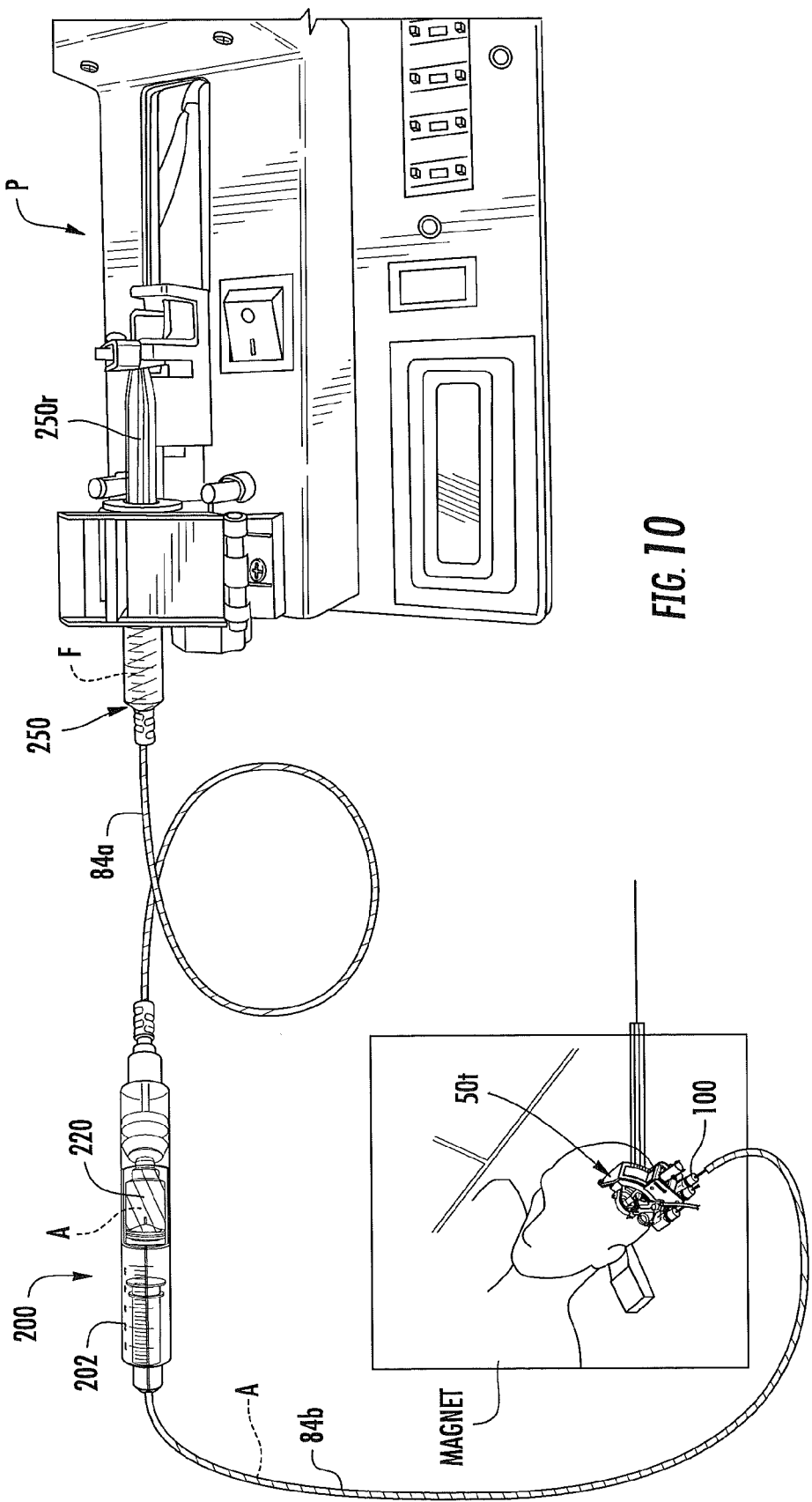
FIG. 10 illustrates a fluid substance delivery system, according to some embodiments of the present invention.

The lumen 112 is fluidly connected to the substance delivery device 200 via tubing 84b (FIGS. 1 and 10), and the drug delivery device 200 is fluidly connected to the pump P via tubing 84a (FIGS. 1 and 10). The tubing 84a, 84b may be flexible tubing. According to some embodiments, the tubing 84a, 84b is PVC tubing. According to some embodiments, the tubing 84a, 84b is silicone tubing. The tubing 84a, 84b may have various lengths. For example, in some embodiments, the tubing may be six to ten feet (6 ft-10 ft) in length, although other lengths are possible. Typically, tubing 84b is considerably shorter than tubing 84a in order to reduce the distance the substance A has to travel to the cannula 100 and thereby reduce volume thereof that is wasted. For example, the tubing 84b may be only a few inches in length in some embodiments. In other embodiments, the tubing 84b is eliminated altogether and the substance delivery device 200 is connected directly to the cannula 100 (e.g., a rigid part of an infusion cannula, catheter, biopsy needle, etc.).

As will be described further below, the pump P is configured to move the push rod 250r of a syringe 250 containing a slave fluid F such that the slave fluid is forced out of the syringe 250. The resulting pressure of the slave fluid F causes the plunger assembly 230 within the substance delivery device 200 to move which, in turn causes the cartridge diaphragm 224 to be pierced by the needle 240 and the substance A forced out of the cartridge 220 and through the needle 240.

The substance (A, FIG. 2) delivered to the target region through the delivery cannula 100 may be any suitable and desired substance. According to some embodiments, substance A is a liquid or slurry. In the case of a tumor, the substance A may be a chemotherapeutic (cytotoxic) fluid. In some embodiments, the substance A can include certain types of advantageous cells that act as vaccines or other medicaments (for example, antigen presenting cells such as dentritic cells). The dentritic cells may be pulsed with one or more antigens and/or with RNA encoding one or more antigen. Exemplary antigens are tumor-specific or pathogen-specific antigens. Examples of tumor-specific antigens include, but are not limited to, antigens from tumors such as renal cell tumors, melanoma, leukemia, myeloma, breast cancer, prostate cancer, ovarian cancer, lung cancer and bladder cancer. Examples of pathogen-specific antigens include, but are not limited to, antigens specific for HIV or HCV. In some embodiments, the substance A may comprise radioactive material such as radioactive seeds. Substances A delivered to a target area in accordance with embodiments of the present invention may include, but are not limited to, the following drugs (including any combinations thereof) listed in Table 1. Exemplary disorders that can be treated by the various drugs are also listed in Table 1.

TABLE 1

| DRUG (generic name) | DISORDER(S) |
| --- | --- |
| Caprylidene | Alzheimer's disease |
| Donepezil | Alzheimer's disease |
| Galantamine | Alzheimer's disease |
| Memantine | Alzheimer's disease |
| Tacrine | Alzheimer's disease |
| vitamin E | Alzheimer's disease |
| ergoloid mesylates | Alzheimer's disease |
| Riluzole | Amyotrophic lateral sclerosis |
| Metoprolol | Benign essential tremors |
| Primidone | Benign essential tremors |
| Propanolol | Benign essential tremors |
| Gabapentin | Benign essential tremors & Epilepsy |
| Nadolol | Benign essential tremors & Parkinson's disease |
| Zonisamide | Benign essential tremors & Parkinson's disease |
| Carmustine | Brain tumor |
| Lomustine | Brain tumor |
| Methotrexate | Brain tumor |
| Cisplatin | Brain tumor & Neuroblastoma |
| Ioversol | Cerebral arteriography |
| Mannitol | Cerebral Edema |
| Dexamethasone | Cerebral Edema & Neurosarcoidosis |
| Baclofen | Cerebral spasticity |
| Ticlopidine | Cerebral thrombosis/embolism |
| Isoxsuprine | Cerebrovascular insufficiency |
| Cefotaxime | CNS infection & Meningitis |
| Acyclovir | Encephalitis |
| Foscarnet | Encephalitis |
| Ganciclovir | Encephalitis |
| interferon alpha-2a | Encephalitis |
| Carbamazepine | Epilepsy |
| Clonazepam | Epilepsy |
| Diazepam | Epilepsy |
| divalproex sodium | Epilepsy |
| Ethosuximide | Epilepsy |
| Ethotoin | Epilepsy |
| Felbamate | Epilepsy |
| Fosphenytoin | Epilepsy |
| Levetiracetam | Epilepsy |
| Mephobarbital | Epilepsy |
| Paramethadione | Epilepsy |
| Phenytoin | Epilepsy |
| Trimethadione | Epilepsy |
| Pregabalin | Epilepsy & Neuralgia |
| immune globulin intravenous | Guillain-Barre Syndrome |
| interferon beta-1b | Guillain-Barre Syndrome & Multiple sclerosis |
| Azathioprine | Guillain-Barre Syndrome & Multiple sclerosis & Neurosarcoidosis |
| Risperidone | Head injury |
| Tetrabenazine | Huntington's disease |
| Acetazolamide | Hydrocephalus & Epilepsy |
| Alteplase | Ischemic stroke |
| Clopidogrel | Ischemic stroke |
| Nimodipine | Ischemic stroke & Subarachnoid hemorrhage |
| Aspirin | Ischemic stroke & Thromboembolic stroke |
| Amikacin | Encaphalitis |
| Ampicillin | Encaphalitis |
| ampicillin/sulbactam | Encaphalitis |
| Ceftazidime | Encaphalitis |
| Ceftizoxime | Encaphalitis |
| Cefuroxime | Encaphalitis |
| Chloramphenicol | Encaphalitis |
| cilastatin/imipenem | Encaphalitis |
| Gentamicin | Encaphalitis |
| Meropenem | Encaphalitis |
| Metronidazole | Encaphalitis |

TABLE 1-continued

| DRUG (generic name) | DISORDER(S) |
|---|---|
| Nafcillin | Encaphalitis |
| Oxacillin | Encaphalitis |
| Piperacillin | Encaphalitis |
| Rifampin | Encaphalitis |
| sulfamethoxazole/trimethoprim | Encaphalitis |
| Tobramycin | Encaphalitis |
| Triamcinolone | Encaphalitis |
| Vancomycin | Encaphalitis |
| Ceftriaxone | Encaphalitis & Neurosyphilis |
| Penicillin | Encaphalitis & Neurosyphilis |
| Corticotrophin | Multiple sclerosis |
| Dalfampridine | Multiple sclerosis |
| Glatiramer | Multiple sclerosis |
| Mitoxantrone | Multiple sclerosis |
| Natalizumab | Multiple sclerosis |
| Modafinil | Multiple sclerosis |
| Cyclophosphamide | Multiple sclerosis & Brain tumor & Neuroblastoma |
| interferon beta-1a | Multiple sclerosis & Neuritis |
| Prednisolone | Multiple sclerosis & Neurosarcoidosis |
| Prednisone | Multiple sclerosis & Neurosarcoidosis |
| Amantadine | Multiple sclerosis & Parkinson's disease |
| Methylprednisolone | Neuralgia |
| Desvenlafaxine | Neuralgia |
| Nortriptyline | Neuralgia |
| Doxorubicin | Neuroblastoma |
| Vincristine | Neuroblastoma |
| Albendazole | Neurocystecercosis |
| chloroquine phosphate | Neurosarcoidosis |
| Hydroxychloroquine | Neurosarcoidosis |
| Infliximab | Neurosarcoidosis |
| Pentoxyfilline | Neurosarcoidosis |
| Thalidomide | Neurosarcoidosis |
| Apomorphine | Parkinson's disease |
| Belladonna | Parkinson's disease |
| Benztropine | Parkinson's disease |
| Biperiden | Parkinson's disease |
| Bromocriptine | Parkinson's disease |
| Carbidopa | Parkinson's disease |
| carbidopa/entacapone/levodopa | Parkinson's disease |
| carbidopa/levodopa | Parkinson's disease |
| Entacapone | Parkinson's disease |
| Levodopa | Parkinson's disease |
| pergolide mesylate | Parkinson's disease |
| Pramipexole | Parkinson's disease |
| Procyclidine | Parkinson's disease |
| Rasagiline | Parkinson's disease |
| Ropinirole | Parkinson's disease |
| Rotiotine | Parkinson's disease |
| Scopolamine | Parkinson's disease |
| Tolcapone | Parkinson's disease |
| Trihexyphenidyl | Parkinson's disease |
| Seleginline | Parkinson's disease |
| Rivastigmine | Parkinson's disease & Alzheimer's disease |
| Anisindione | Thromboembolic stroke |
| Warfarin | Thromboembolic stroke |
| 5-hydroxytryptophan | Depression & Anxiety & ADHD |
| Duloxetine | Depression & Anxiety & Bipolar disorder |
| Escitalopram | Depression & Anxiety & Bipolar disorder |
| Venlafaxine | Depression & Anxiety & Bipolar disorder & Autism & Social anxiety disorder |
| Desvenlafaxine | Depression & Anxiety & PTSD & ADHD |
| Paroxetine | Depression & Anxiety & PTSD & Social anxiety disorder |
| fluoxetine/olanzapine | Depression & Bipolar disorder |
| l-methylfolate | Depression & BPD |
| Amitriptyline | Depression & PTSD |
| Sertraline | Depression & PTSD & Bipolar disorder & Social anxiety disorder |
| Fluvoxamine | Depression & PTSD & Social anxiety disorder |
| Olanzapine | Depression & Schizophrenia & Bipolar disorder |
| Paliperidone | Depression & Schizophrenia & Bipolar disorder |
| Aripiprazole | Depression & Schizophrenia & Bipolar disorder & Autism |
| Quetiapine | Depression & Schizophrenia & PTSD & BPD & Bipolar disorder |
| Risperidone | Depression & Schizophrenia & PTSD & BPD & Bipolar disorder & Autism |
| Amisulpride | Depression & Social anxiety disorder |
| Chlorpromazine | Psychosis |
| Droperidol | Psychosis |

TABLE 1-continued

| DRUG (generic name) | DISORDER(S) |
|---|---|
| Fluphenazine | Psychosis |
| Periciazine | Psychosis |
| Perphenazine | Psychosis |
| Thiothixene | Psychosis |
| Triflupromazine | Psychosis |
| Haloperidol | Psychosis & Dementia |
| Prazosin | PTSD |
| Clozapine | Schizophrenia |
| Flupenthixol | Schizophrenia |
| Iloperidone | Schizophrenia |
| Loxapine | Schizophrenia |
| Mesoridazine | Schizophrenia |
| Promazine | Schizophrenia |
| Reserpine | Schizophrenia |
| Thioridazein | Schizophrenia |
| Zuclopenthixol | Schizophrenia |
| Asenapine | Schizophrenia & Bipolar disorder |
| Levomepromazine | Schizophrenia & Bipolar disorder |
| Ziprasidone | Schizophrenia & Bipolar disorder |
| Molindone | Schizophrenia & Psychosis |
| Pimozide | Schizophrenia & Psychosis |
| Thioridazine | Schizophrenia & Psychosis |
| Cytarabine | Chemotherapy, hematological malignancies |

Referring now to FIGS. 3-10, a substance delivery device 200 for use with the fluid substance delivery system 80 of FIGS. 1-2 is illustrated. The substance delivery device 200 includes a tubular body 202 having a hollow interior 202i, open proximal and distal ends 204, 206, and a longitudinal opening or window 210 located between the proximal and distal ends 204, 206. The tubular body 202 may be formed from various materials including, but not limited to, glass and polymeric material, and may be formed from MRI-compatible material. The longitudinal opening 210 is adapted to allow a substance cartridge 220 (FIG. 7C) to be inserted within the tubular body 202. The substance cartridge 200 can be a single use cartridge or a reusable (e.g., a refillable, multi-use cartridge). A plunger assembly 230 is slidably received within the hollow interior 202i proximate the tubular body proximal end 204, as illustrated.

The longitudinal opening 210 may have various shapes and configurations, without limitation. In some embodiments, a door or cover (not shown) may be provided to close the longitudinal opening 210 after a substance cartridge 220 has been inserted therethrough and into the tubular body 202 of the substance delivery device 200.

Figure 3:
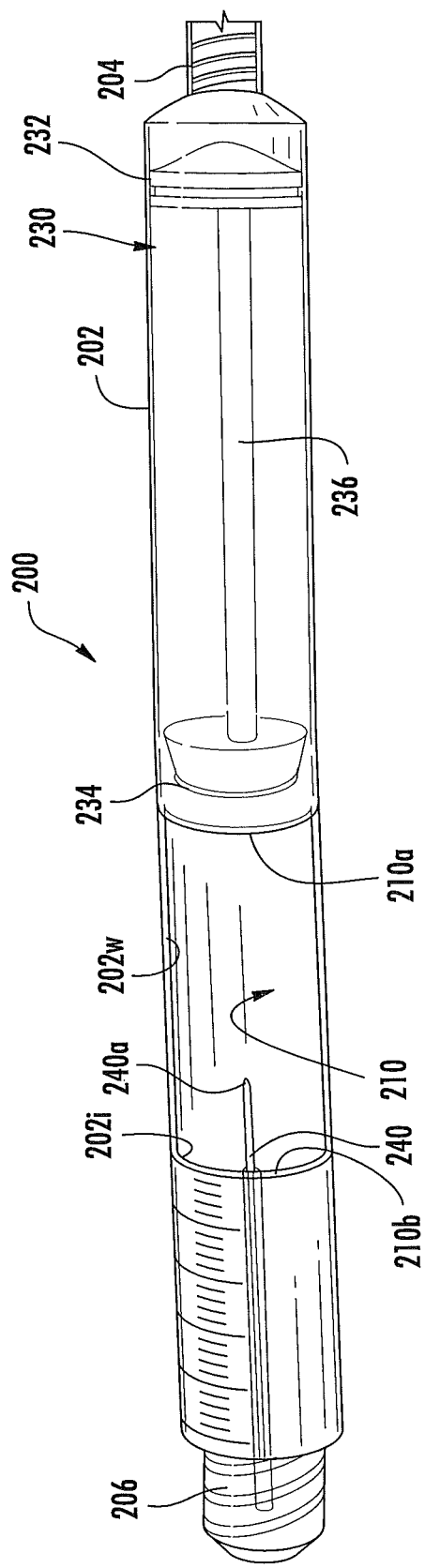
FIG. 3 is a perspective view of a substance delivery device, according to some embodiments of the present invention.

The plunger assembly 230 includes a plunger 232 that is in slideable sealing engagement with an inside wall 202w of the tubular body 202, an engagement head 234, and a rod 236 that extends between and connects the plunger 232 and engagement head 234. In some embodiments, the plunger 232 is formed from an elastomeric material. As illustrated in FIG. 3 and FIG. 7C, the plunger assembly 230 is positioned within the tubular body 202 such that the engagement head 234 is positioned proximate a first end portion 210a of the longitudinal opening 210 so as to allow a substance cartridge 220 to be inserted within the longitudinal opening 210.

A hollow needle 240 is secured within the hollow interior 202i proximate the tubular body distal end 206. The needle 240 includes a piercing end 240a that is configured to pierce a diaphragm 224 (FIG. 7B, 8) of a substance cartridge 220, as will be described below. The needle piercing end 240a is positioned proximate a second end portion 210b of the longitudinal opening 210 so as to allow a substance cartridge 220 to by inserted within the longitudinal opening 210. The needle 240 includes an opposite end 240b (FIG. 7C) that is in fluid communication with the distal end 206 of the tubular body 202. As will be described below, the needle piercing end 240a pierces a diaphragm 224 of a substance cartridge 220 and the substance A within the cartridge 220 is forced out of the cartridge 220 through the needle 240, and out the distal end 206 of the tubular body 202.

Figure 9:
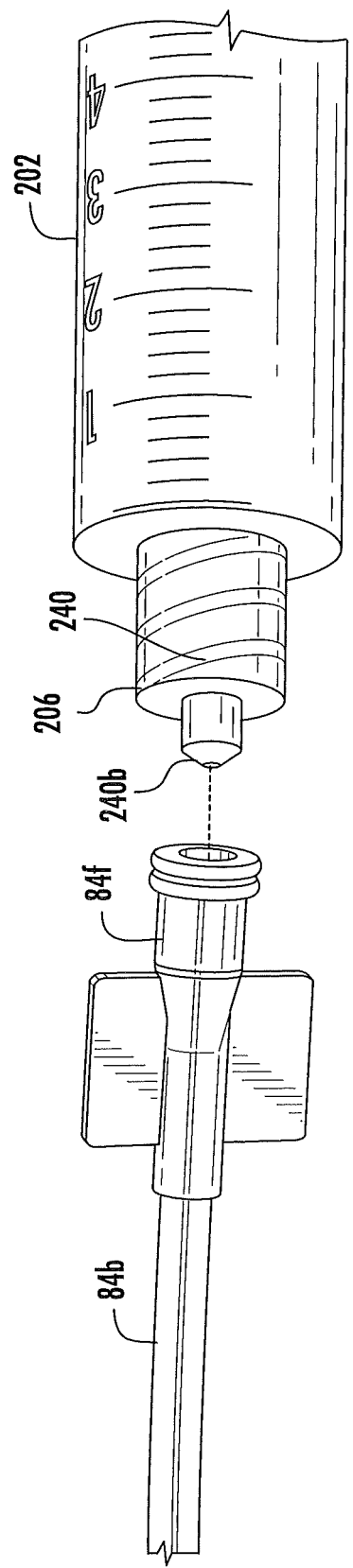
FIG. 9 is a partial view of the substance delivery device of FIG. 3 and illustrating tubing that can be secured to the distal end of the substance delivery device.

Referring to FIG. 9, tubing 84b is adapted to be secured to the tubular body distal end 206 via a fitting 84f that matingly engages the distal end 206. For example, the fitting 84f may be a threaded connector, such as a Luer lock connector, that threadingly engages corresponding threads on the distal end 206. A substance A flowing through the needle 240 from a substance cartridge 220 flows into the tubing 84b and on to a cannula 100 for injection into a patient (FIG. 10). In addition, the tubular body distal end 206 may be configured to be connected directly to the cannula 100 or to another device (e.g., a catheter or biopsy needle, etc.).

Referring to FIGS. 7A-7B, an exemplary substance cartridge 220 that is configured to be inserted within the tubular body 202, via the longitudinal opening 210 therein, is illustrated. The substance cartridge 220 has a tubular body 222 with opposite proximal and distal ends 222a, 222b. The tubular body 222 of the cartridge 220 may be formed from various materials including, but not limited to, glass and polymeric material, and may be formed from MRI-compatible material. The tubular body 222 may be sized to receive different volumes of a substance A. The substance A is sealed within the body 222 via a diaphragm 224 at the proximal end 222a and a cap 226 at the distal end 222b.

Referring to FIG. 10, the substance A within the cartridge 220 is forced out of the cartridge 220 via a slave fluid F contained within the syringe 250 and tubing 84a upstream from the substance delivery device 200. The syringe 250 is mounted within a pump P that is configured to push a plunger rod 250r of the syringe 250. When the plunger rod 250r is pushed by the pump P, the slave fluid F causes the plunger assembly 230 (FIG. 7C) in the substance delivery device 200 to drive the substance cartridge 220 therein such that the needle piercing end 240a pierces the cartridge diaphragm 224. The pressure from the slave fluid F further causes the substance A to flow downstream through the tubing 84*b* and into the cannula 100.

Figure 4C:
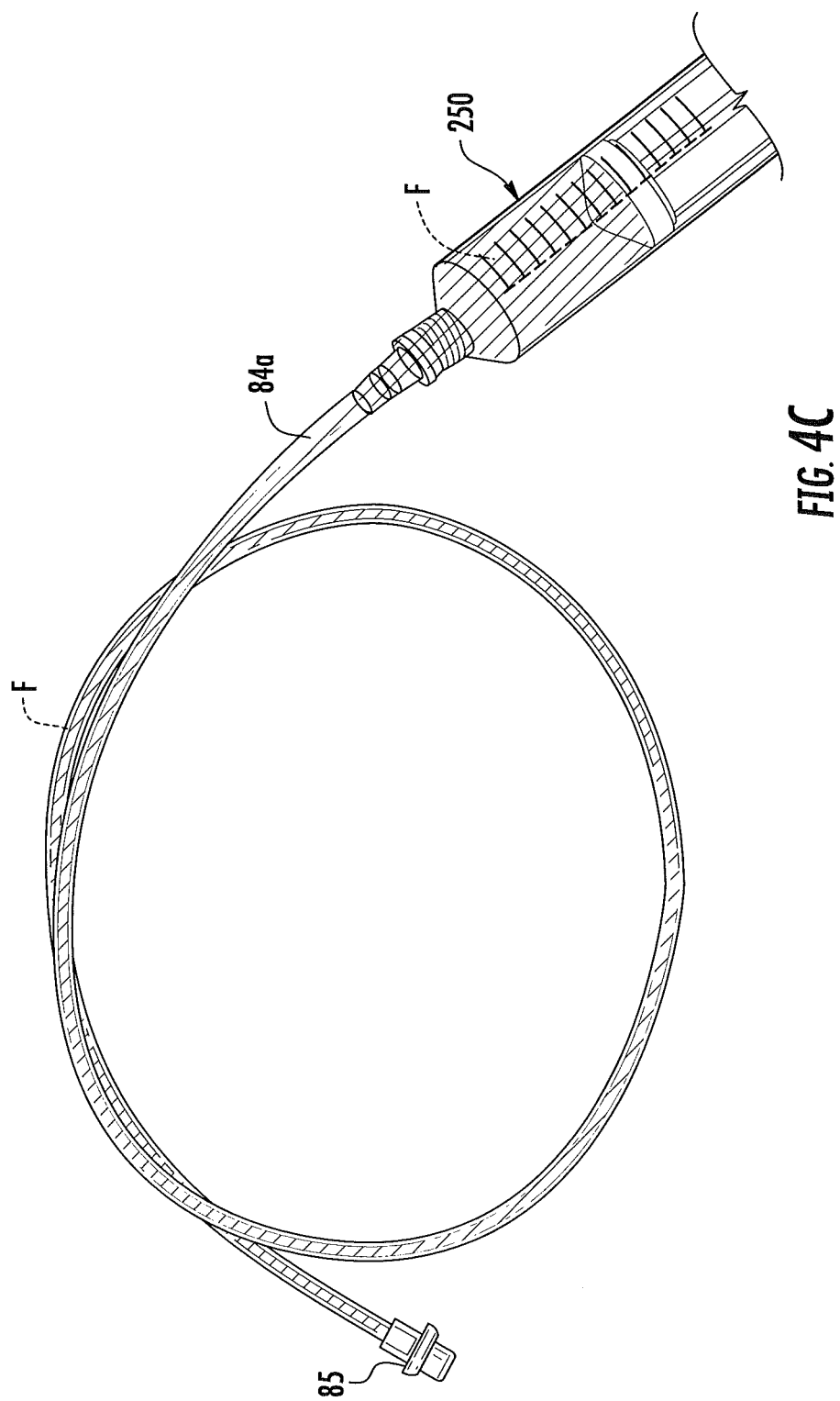

Referring now to FIGS. 4A-4C, 5A-5B, 6A-6C and 7A-7B, operations for preparing a substance for delivery into a patient are illustrated. These preparatory operations can be carried out on site or can be performed remotely and a drug delivery device 200 and cartridge 220 filled with a substance A can be provided as a sterile package ready for use and with a defined shelf life. In FIG. 4A, a technician draws a slave fluid F, such as a saline solution, etc., into syringe 250, as would be understood by one skilled in the art. The slave fluid F can be virtually any type of fluid and typically is a fluid, such as saline, that is not harmful if injected into a patient. In FIG. 4B, the technician removes any air bubbles from the slave fluid F in the syringe 250, as would be understood by one skilled in the art. In FIG. 4C, tubing 84*a* is connected to the syringe 250 and has been filled with the slave fluid F, and such that no bubbles are contained therein.

Figure 5A:
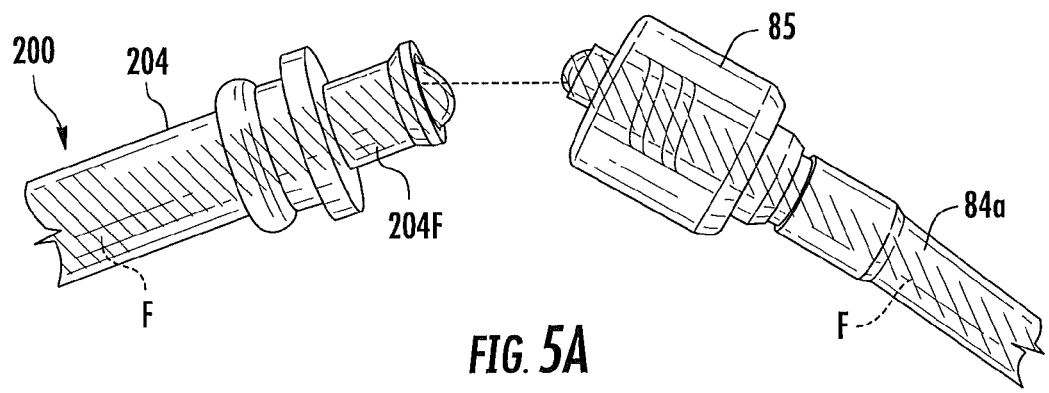
Figure 5B:
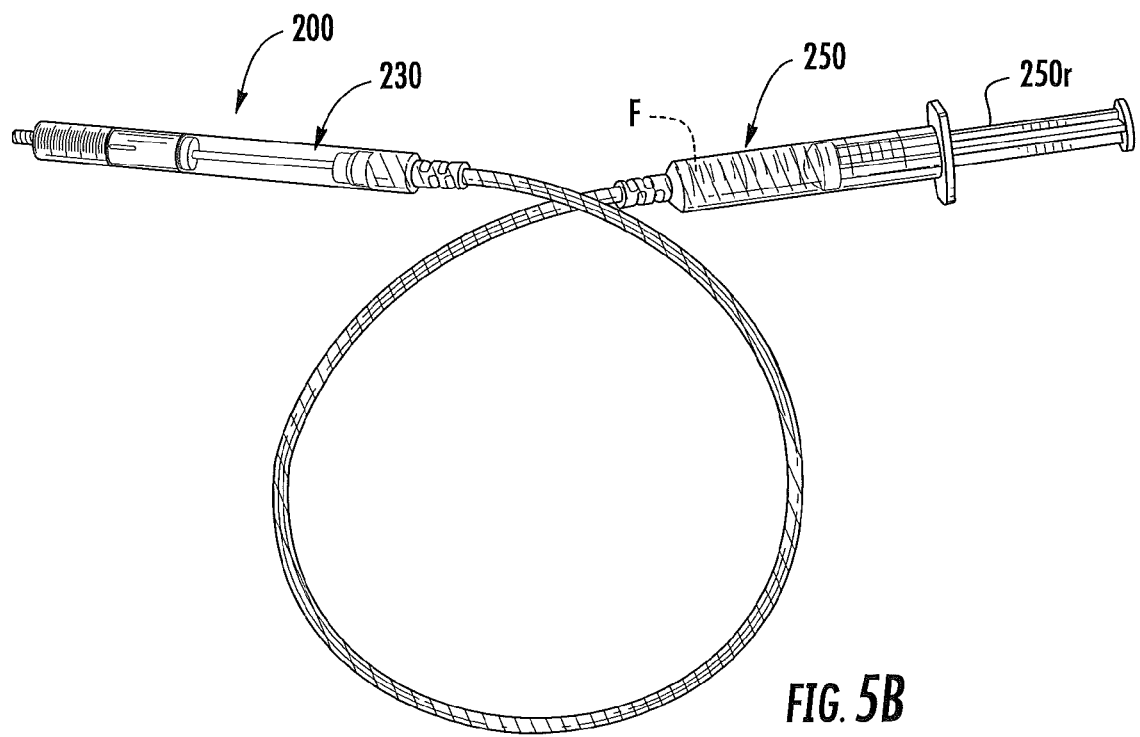

In FIG. 5A, the proximal end 204 of the tubular body 202 of the substance delivery device 200 upstream from the plunger 232 has been filled with the slave fluid F such that no air bubbles are contained therein. The tubing 84*a* is then connected to the substance delivery device 200 via a connector 85*f* that matingly engages (typically via threaded connectors) with a connector 204*f* at the tubular body proximal end 204. FIG. 5B illustrates the syringe 250 and tubing 84*a* containing the slave fluid F attached to the substance delivery device 200 and without any air bubbles therein. User (or pump) movement of the plunger rod 250*r* of the syringe 250 thereby causes movement of the plunger assembly 230 in the substance delivery device 200.

Figure 6A:
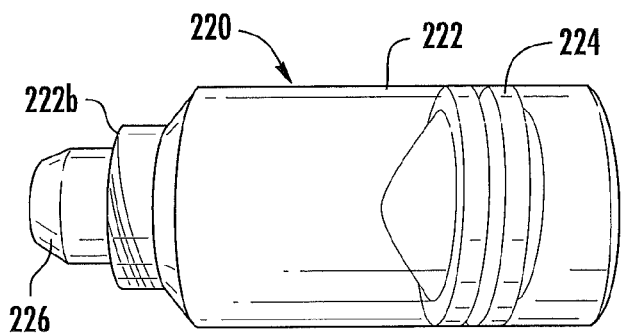
Figure 6B:
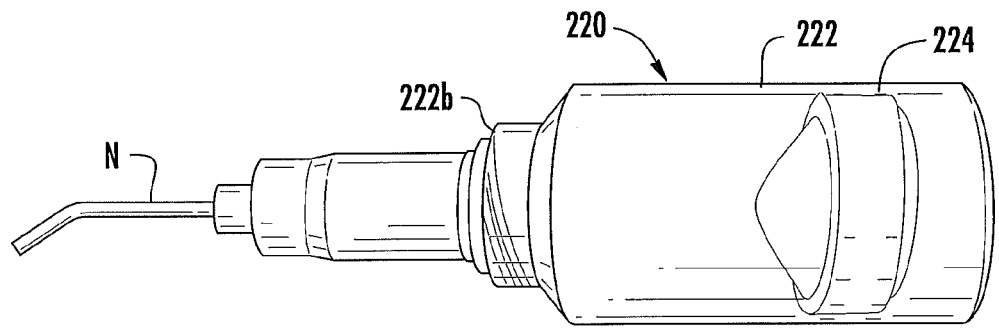
Figure 6C:
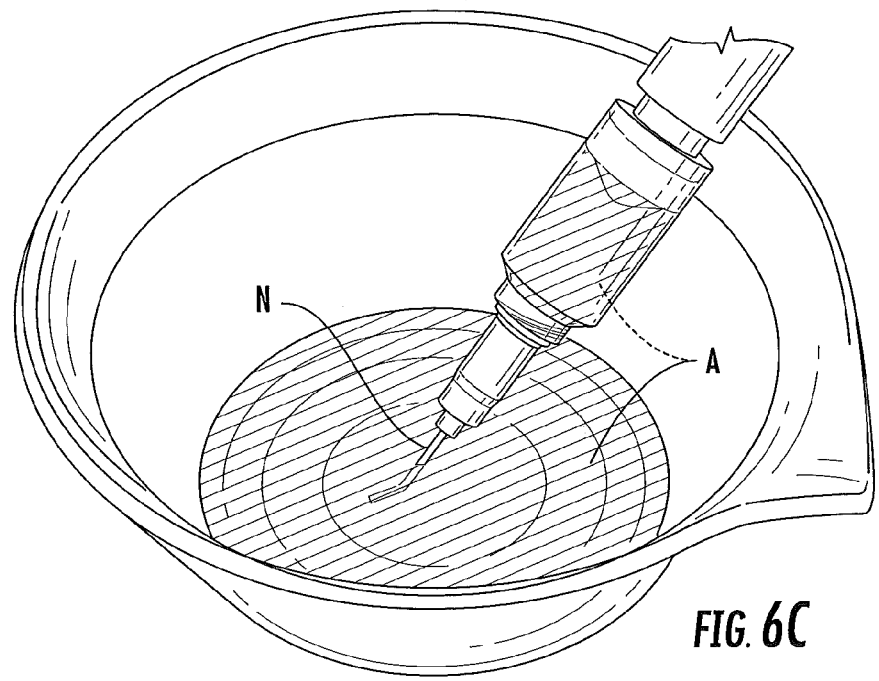

In FIG. 6A, an unfilled substance cartridge 220 (single use or multiple use) is illustrated. In FIG. 6B, the cap 226 has been removed from the distal end 222*b* and a needle N has been placed thereon. The cap may be a threaded cap. In FIG. 6C, a technician draws a substance A into the cartridge 220, for example, via a syringe. In some embodiments, the cartridge diaphragm 224 has a threaded portion that allows a correspondingly threaded rod, such as a syringe plunger rod, to be inserted through the proximal end 222*a* and become matingly engaged with the diaphragm 224. The technician can use the connected rod to pull the diaphragm 224 from the distal end 222*b* towards the proximal end 222*a* of the cartridge 220 and draw the substance A into the cartridge 220.

In FIG. 7A, the technician removes air bubbles from the substance A within the cartridge 220, as would be understood by one skilled in the art. In FIG. 7B, the filled cartridge 220 distal end 222*b* is sealed with a cap 226 and the cartridge 220 is ready for insertion within the substance delivery device 200. Cartridges 220 that are utilized with embodiments of the present invention can have various sizes. For example, cartridges 220 may be sized to hold less than twenty microliters (20 μL) of a substance A, twenty microliters (20 μL) or more of a substance A, etc. An exemplary range of cartridge volumes is between about twenty microliters (20 μL) and about thirty milliliters (30 cc); however, other ranges are possible without limitation.

In FIG. 7C, the filled cartridge 220 has been placed within the tubular body 202 of the substance delivery device 200 via the longitudinal opening 210. As illustrated, the piercing end 240*a* of the needle 240 and the engagement head 234 of the plunger assembly 230 are positioned proximate the longitudinal opening such that they do not interfere with insertion of the cartridge 220. In FIG. 8, the slave fluid F (not shown) has pushed the plunger assembly 230 such that the engagement head 234 has engaged the cartridge 220 at the cap 226 and has pushed the cartridge 220 such that the piercing end 240*a* of the needle 240 has penetrated the diaphragm 224. At this point, the substance A is forced through the needle 240 and through the downstream tubing 84*b* (if used), as described above.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A substance delivery device, comprising:
    an elongated tubular body comprising opposing proximal and distal ends, and a longitudinal opening having opposing first and second ends located between and spaced apart from both the tubular body proximal and distal ends that is adapted to receive a substance cartridge;
    a plunger assembly in slideable engagement with an inside wall of the tubular body proximate the proximal end thereof;
    a hollow needle extending axially inside the tubular body proximate the distal end thereof, wherein the needle comprises a piercing end positioned proximate the second end of the longitudinal opening and an opposite end, and wherein the hollow needle is in fluid communication with the tubular body distal end via the opposite end; and
    a cannula comprising a cannula body defining at least one longitudinally extending lumen, an inlet port, and at least one exit port, wherein the at least one longitudinally extending lumen is fluidly connected to the tubular body distal end via flexible tubing, and wherein the cannula is adapted to transfer a substance from the substance cartridge to a selected region in a patient via the at least one exit port when the hollow needle piercing end pierces a portion of the substance cartridge.

2. The device of claim 1, wherein the plunger assembly comprises a plunger that is in slideable sealing engagement with the inside wall of the tubular body, an engagement head positioned proximate the second end of the longitudinal opening, and a rod extending between and connecting the plunger and engagement head.

3. The device of claim 2, wherein the tubular body, plunger assembly, hollow needle, and cannula comprise MRI-compatible material.

4. The device of claim 1, wherein an exterior surface of the cannula has at least first and second co-axially disposed segments having different outer diameters.

5. The device of claim 4, wherein the exterior surface includes a tapered transition between the first and second segments.

6. A system for delivering a substance to a patient, the system comprising:
    a substance delivery device, comprising:
        a tubular body comprising opposing proximal and distal ends, and a longitudinal opening having opposing first and second ends located between and spaced apart from both the tubular body proximal and distal ends;

a plunger assembly in slideable engagement with an inside wall of the tubular body proximate the proximal end thereof; and a hollow needle secured within the tubular body proximate the distal end thereof, wherein the hollow needle comprises a piercing end positioned proximate an end of the longitudinal opening and an opposite end, and wherein the hollow needle is in fluid communication with the tubular body distal end via the opposite end;

a substance cartridge containing a substance and having opposing proximal and distal ends, wherein a diaphragm is slidably secured within the cartridge to seal the substance therewithin, wherein the substance cartridge is positioned within the longitudinal opening such that the diaphragm faces the hollow needle piercing end;

a cannula comprising a cannula body defining at least one longitudinally extending lumen, an inlet port, and at least one exit port, wherein the at least one longitudinally extending lumen is fluidly connected to the tubular body distal end via flexible tubing, and wherein the cannula is adapted to transfer a substance from the substance cartridge to a selected region in a patient via the at least one exit port when the hollow needle piercing end pierces the substance cartridge diaphragm; and a syringe in fluid communication with the tubular body proximal end, wherein the syringe contains a slave fluid, and wherein activation of the syringe causes the slave fluid to move the substance cartridge via the plunger assembly such that the diaphragm is pierced by the hollow needle piercing end.

7. The system of claim 6, wherein the cannula is MRI-compatible.

8. The system of claim 6, wherein the substance delivery device and substance cartridge comprise MRI-compatible material.

9. The system of claim 6, wherein the plunger assembly comprises a plunger that is in slideable sealing engagement with the inside wall of the tubular body, an engagement head positioned proximate to the first end of the longitudinal opening, and a rod extending between and connecting the plunger and engagement head.

10. The system of claim 6, further comprising a pump adapted to activate the syringe and cause the slave fluid to eject a substance from the substance cartridge positioned within the tubular body.

11. The system of claim 6, wherein the substance cartridge is a single use substance cartridge.

12. The system of claim 6, wherein the at least one longitudinally extending lumen is fluidly connected to the tubular body distal end via first flexible tubing having a first length, and wherein the syringe is in fluid communication with the tubular body proximal end via second flexible tubing having a second length that is substantially greater than the first length.

13. The system of claim 12, wherein the second length is at least about six feet (6 ft).

14. The system of claim 6, wherein an exterior surface of the cannula has at least first and second co-axially disposed segments having different outer diameters.

15. The system of claim 14, wherein the exterior surface includes a tapered transition between the first and second segments.

16. A method for delivering a substance to a patient in an MRI-guided surgical procedure, the method comprising:

inserting a cannula into a selected region of the patient, wherein the cannula comprises a cannula body defining at least one longitudinally extending lumen, an inlet port, and at least one exit port, wherein the at least one longitudinally extending lumen is in fluid communication with a substance delivery device containing the substance, wherein the substance delivery device comprises:

a tubular body having opposing proximal and distal ends, and a longitudinal opening having opposing ends located between and spaced apart from both the tubular body proximal and distal ends;

a plunger assembly in slideable engagement with an inside wall of the tubular body proximate the proximal end thereof;

a hollow needle secured within the tubular body proximate the distal end thereof, wherein the needle comprises a piercing end positioned proximate an end of the longitudinal opening and an opposite end, and wherein the hollow needle is in fluid communication with tubular body distal end; and flexible tubing fluidly connecting the tubular body distal end with the cannula body inlet port;

wherein a substance cartridge containing the substance is positioned within the tubular body longitudinal opening, wherein the substance cartridge has opposing proximal and distal ends, wherein a diaphragm is slidably secured within the cartridge to seal the substance therewithin, and wherein the substance cartridge is positioned within the longitudinal opening such that the diaphragm faces the hollow needle piercing end, and wherein a syringe is in fluid communication with the tubular body proximal end, and wherein the syringe contains a slave fluid; and transferring the substance from the substance delivery device to the selected region through the at least one longitudinally extending lumen by activating the syringe to cause the slave fluid to move the substance cartridge via the plunger assembly such that the diaphragm is pierced by the hollow needle piercing end.

17. The method of claim 16, wherein activating the syringe to cause the slave fluid to move the substance cartridge comprises activating the syringe via a pump.

18. The method of claim 16, wherein the tubular body distal end is fluidly connected with the cannula body inlet port via first flexible tubing having a first length, and wherein the syringe is in fluid communication with the tubular body proximal end via second flexible tubing having a second length that is substantially greater than the first length.

19. The method of claim 16, wherein an exterior surface of the cannula has at least first and second co-axially disposed segments having different outer diameters.

20. The method of claim 19, wherein the exterior surface includes a tapered transition between the first and second segments.

* * * * *